United States Patent [19]

Wirz et al.

[11] Patent Number: 4,565,450

[45] Date of Patent: Jan. 21, 1986

[54] ARRANGEMENT FOR AND METHOD OF DETERMINING THE AMOUNT OF DAMPENING AGENT ON A PRINTING-IMAGE CARRIER

[75] Inventors: Burkhardt Wirz, Munich; Rainer Kammüller, Wilnsdorf-Obersdorf, both of Fed. Rep. of Germany

[73] Assignee: Grapho Metronic Mess- und Regeltechnik GmbH & Co. KG, Munich, Fed. Rep. of Germany

[21] Appl. No.: 497,828

[22] Filed: May 25, 1983

[30] Foreign Application Priority Data

May 28, 1982 [DE] Fed. Rep. of Germany ....... 3220282

[51] Int. Cl.$^4$ .......................... G01J 3/50; B41L 25/00
[52] U.S. Cl. .................... 356/402; 356/414; 356/416; 356/446; 101/148
[58] Field of Search ................ 356/23, 300, 402, 407, 356/414, 416, 425, 432, 433, 434, 436, 440, 445, 446, 447, 448; 101/147, 148, 350

[56] References Cited

U.S. PATENT DOCUMENTS

| | | | |
|---|---|---|---|
| 3,439,175 | 4/1969 | Kammüller et al. | 356/382 |
| 3,599,002 | 9/1969 | Beutelspacher | 356/23 |
| 3,748,046 | 7/1973 | Murray | 101/350 |
| 3,832,065 | 8/1974 | Sullivan et al. | 356/447 |
| 3,874,799 | 4/1975 | Isaacs et al. | 356/407 |
| 3,960,451 | 6/1976 | Wirz et al. | 356/434 |
| 4,052,937 | 10/1977 | Lawson et al. | 356/445 |
| 4,124,803 | 11/1978 | Bowers | 356/448 |
| 4,290,698 | 9/1981 | Milana | 356/448 |
| 4,360,275 | 11/1982 | Louderback | 356/446 |
| 4,407,197 | 10/1983 | Jeschke | 101/148 |
| 4,455,090 | 6/1984 | Roberts | 356/448 |

FOREIGN PATENT DOCUMENTS 2064113 6/1981 United Kingdom ............... 356/402

Primary Examiner—R. A. Rosenberger
Assistant Examiner—Joel L. Harringa
Attorney, Agent, or Firm—Peter K. Kontler

[57] ABSTRACT

Radiation pulses are directed at a measuring spot on a rotating printing-image carrier in an offset printing press. The intensity of the radiation returned from the measuring spot outside of the angle of reflection of the pulse is measured for a predetermined wavelength. A pulse is directed at the measuring spot before printing and while the measuring spot is dry, and a signal representing the intensity of the returned radiation is stored in a working memory. During a subsequent printing operation, a dampening agent is applied to the printing-image carrier. In order to determine the amount of dampening agent on the printing-image carrier, radiation pulses are directed at the measuring spot as the printing-image carrier rotates during printing. The intensity of the returned radiation in the predetermined wavelength is converted into damp signals which represent the amount of dampening agent since the predetermined wavelength approximates or equals an absorption wavelength of the dampening agent. The damp signals are related to the stored dry signal in a computer to yield values indicative of the amount of dampening agent on the printing-image carrier.

32 Claims, 4 Drawing Figures

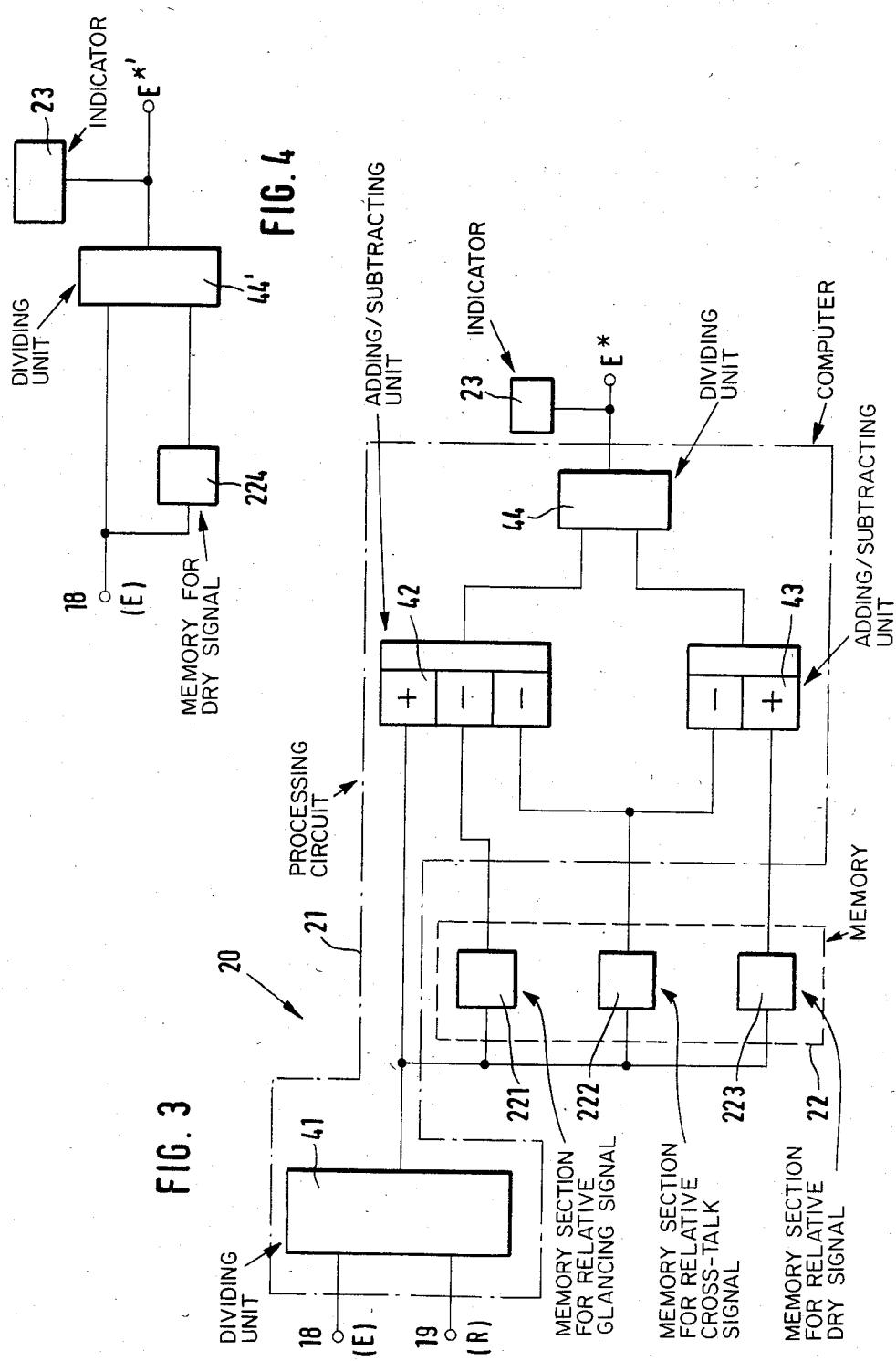

ARRANGEMENT FOR AND METHOD OF DETERMINING THE AMOUNT OF DAMPENING AGENT ON A PRINTING-IMAGE CARRIER

BACKGROUND OF THE INVENTION

The invention relates generally to an arrangement for and a method of determining the amount of dampening agent on a printing-image carrier.

More particularly, the invention relates to an arrangement for and a method of determining the amount of dampening agent on a rotating printing-image carrier during a printing operation, especially a printing-image carrier of an offset printing press.

A known arrangement for determining the amount of dampening agent on a rotating printing-image carrier in an offset printing press has a radiation source which directs pulses of radiation at a measuring spot or region of the carrier. The radiation includes radiation of a wavelength which at least approximates the absorption wavelength of the dampening agent. Radiation returned from the carrier outside of the angle of reflection of the radiation directed at the carrier is guided through a photoelectric transducer. The latter quantitatively converts the returned radiation pulses into electrical signals. These signals are processed in a processing circuit to yield a value representative of the amount of dampening agent which is present on the carrier.

An arrangement of this type is disclosed, for example, in the German Pat. No. 1 303 819. The arrangement of the German Patent employs radiation pulses in which the wavelengths lie within an absorption band of the dampening agent as well as additional radiation pulses in which the wavelengths are located in a range which is presumably only minimally affected by the dampening agent. The amplitudes of the pulses of different wavelength are differently affected by the dampening agent and quotients are formed from the amplitudes of the pulses of different wavelength. The quotients are represented by electrical signals which are processed in an attempt to draw conclusions regarding the amount of dampening agent present.

At the time the preceding arrangement was designed, it was recognized that the dampening agent affects not only the measuring pulses having wavelengths in the region of the absorption wavelength but also the comparative pulses in which the wavelengths are located outside of the absorption band. Accordingly, a measuring pulse as well as a comparative pulse must be registered during each revolution of the plate cylinder which carries the printing-image carrier so that the pulse amplitudes for each quotient are derived from the same layer of dampening agent. This can be accomplished in two ways. On the one hand, it is possible to have a time lag between generation of the measuring pulse and generation of the comparative pulse. However, when the measuring spot is small and the rotational speed of the plate cylinder is high, the required pulse frequency is hardly attainable with the current state of the art. On the other hand, it is possible to employ separate photoelectric transducers for the measuring pulse and the comparative pulse and to arrange appropriate different filters upstream of the respective transducers. In this case, there is the danger that errors in measurement which are not eliminated by the quotient procedure will arise due to the fact that the transducers have different characteristics, drifts and the like.

It has been further found that, while the effect of the dampening agent on a comparative pulse is small, it is not proportional to the amount of the dampening agent. Unexpected sharp variations occur at relatively large but nevertheless regularly encountered amounts of dampening agent. These variations make it virtually impossible to determine the amount of dampening agent using the conventional quotient procedure.

OBJECTS AND SUMMARY OF THE INVENTION

It is an object of the invention to provide a relatively simple arrangement for determining the amount of dampening agent on a printing-image carrier.

Another object of the invention is to provide a relatively inexpensive arrangement for determining the amount of dampening agent on a printing-image carrier.

An additional object of the invention is to provide an arrangement which is capable of determining the amount of dampening agent on a printing-image carrier with no significant synchronization problems.

A further object of the invention is to provide an arrangement in which the signals for determining the amount of dampening agent on a printing-image carrier are substantially unaffected by irregularities of the type outlined above for the comparative pulses of the prior art arrangements.

It is also an object of the invention to provide an arrangement which makes it possible to readily determine the amount of dampening agent on a printing-image carrier even though the measuring spot is relatively small and/or the carrier rotates at a relatively high speed.

A concomitant object of the invention is to provide an arrangement which makes it possible to determine the amount of dampening agent on a printing-image carrier with a relatively high degree of accuracy.

Yet another object of the invention is to provide a method which makes it possible to determine the amount of dampening agent on a printing-image carrier in a relatively simple manner.

Still a further object of the invention is to provide a method which enables the amount of dampening agent on a printing-image carrier to be determined relatively inexpensively.

An additional object of the invention is to provide a method which makes it possible to determine the amount of dampening agent on a printing-image carrier with substantially no synchronization problems.

It is also an object of the invention to provide a method which makes it possible to determine the amount of dampening agent on a printing-image carrier using signals which are substantially unaffected by irregularities of the type outlined above for the comparative pulses of the prior art arrangements.

Still another object of the invention is to provide a method which enables, the amount of dampening agent on a printing-image carrier to be readily determined even though the measuring spot is relatively small and/or the carrier is rotating at a relatively high speed.

A further object of the invention is to provide a method which makes it possible to determine the amount of dampening agent on a printing-image carrier with a relatively high degree of accuracy.

The preceding objects, as well as others which will become apparent as the description proceeds, are achieved by the invention.

One aspect of the invention resides in an arrangement for determining the amount of dampening agent on a printing-image carrier. The arrangement comprises the following:

(a) A radiation source for directing radiation at the carrier. The radiation source emits at least some radiation having a wavelength which approximates or equals an absorption wavelength of the dampening agent. Preferably, the radiation source is arranged to emit radiation in pulses. The radiation emitted by the radiation source may be directed at a particular measuring spot or region of the carrier.

(b) First means for generating first signals in response to radiation which returns from the carrier and has a wavelength at least approximating the absorption wavelength of the dampening agent. The first means is preferably arranged to detect radiation which returns from the carrier outside of the angle of reflection of the radiation which impinges upon the carrier. Advantageously, the first means includes a photoelectric transducer which quantitatively converts radiation pulses into the first signals.

(c) Second means for generating second signals representative of the amount of dampening agent on the carrier. The second means is arranged to receive the first signals and to relate a preselected first signal generated while the carrier is substantially dry to another first signal generated while the carrier is damp. The second means is designed such that the second signals are derived from the relationship between the preselected and other first signals. Preferably, the second means includes a processing circuit which is capable of processing the first signals and comprises a working memory for storing the preselected first signal.

The arrangement in accordance with the invention may be used to determine the amount of dampening agent on the printing-image carrier as the latter rotates during a printing operation, that is, the amount of dampening agent may be determined while printing is being carried out.

The arrangement of the invention is particularly well-suited for determining the amount of dampening agent on a rotating printing-image carrier in an offset printing press.

Another aspect of the invention resides in a method of determining the amount of dampening agent on a printing-image carrier. The method comprises the following steps:

(a) Irradiating the carrier.

(b) Measuring a characteristic of radiation of a predetermined wavelength returned from the carrier while substantially dry to obtain at least one dry value of the characteristic. The predetermined wavelength at least approximates an absorption wavelength of the dampening agent.

(c) Applying the dampening agent to the carrier.

(d) Measuring the aforesaid characteristic for radiation of the predetermined wavelength returned from the carrier while damp to obtain at least one damp value of the characteristic.

(e) Establishing a relationship between the dry and damp values.

(f) Generating a signal based on this relationship representative of the amount of the dampening agent on the carrier.

It is known that the surface condition of the printing-image carrier affects the return characteristics to a large degree. This is the reason that a measuring pulse and a comparative pulse were previously used for the determination of the amount of dampening agent. It has now been found that a reliable value for the amount of dampening agent can be obtained by sensing only diffuse radiation which is returned from the measuring spot on the carrier and lies in an absorption wavelength range of the dampening agent. The intensity of the diffuse radiation returned in the absorption wavelength range while the carrier is damp is compared with the intensity of the radiation returned in the absorption wavelength range while the carrier is dry. The latter intensity is measured periodically and updated at every opportunity. In other words, before the start of a printing operation, a radiation pulse at least partly constituted by radiation having a wavelength in an absorption wavelength range of the dampening agent is directed at the measuring spot of the printing-image carrier while the measuring spot is dry. Radiation returned from the measuring spot outside of the angle of reflection of the radiation pulse and having a wavelength in the absorption wavelength range is converted into a so-called dry signal by the photoelectric transducer. This dry signal is stored in the working memory of the processing circuit and compared with the electrical signals generated by the transducer during the measuring procedure which is carried out on the dampened printing-image carrier while the printing operation is being performed. A value representative of the amount of dampening agent can then be obtained, e.g., by forming quotients.

The procedure according to the invention is based on a recognition which has been found to be sufficiently precise for at least a number of the common types of printing-image carriers. This recognition resides in that the indicatrices, i.e. the vector field of that portion of the radiation impinging upon a measuring spot which is returned from the latter, are geometrically similar for all measuring locations on a printing-image carrier and for different conditions of wear. Furthermore, the dampening agent causes the indicatrices to undergo geometrically similar reductions. While the magnitudes of the indicatrices at different measuring locations of a dry carrier differ substantially, the relationships between the magnitudes nevertheless remain the same. Thus, by recording the indicatrices in sectors and then forming spatial integrals, it is possible to arrive at a value $E^{*\prime}$, representative of the amount of dampening agent from a quotient or ratio which relates a value $E$ obtained from measurements over damp measuring locations to the stored dry value $E_d$:

$$E^{*\prime} = E/E_d$$

The value $E^{*\prime}$ represents a definite amount of dampening agent.

It is clear that the arrangement and the method according to the invention are substantially simpler than the arrangements and method of the prior art. It is further clear that the value used as a reference is no longer affected by the amount of dampening agent which is present.

It is possible to compensate for errors such as crosstalk which are induced by apparatus components as well as errors due to radiation which glances off the surface of the dampening agent. This may be accomplished by the arrangement of the invention in a known manner using radiation of the same wavelength as is employed to determine the amount of dampening agent. Before the start of a printing operation and, if necessary, during interruptions in the printing operation which may also be used to update the dry value, signals representative of the cross-talk and of the radiation which glances off the dampening agent are generated and stored in the same manner as the dry signal. The cross-talk and glancing signals are then processed together with the damp signals generated by measurement of the dampened printing-image carrier during printing in a manner to be described later.

If the constancy of the radiation source is in question, calculation of the amount of dampening agent can be performed with relative values. To this end, a second photoelectric transducer may be provided. This transducer is arranged to receive radiation pulses from the radiation source directly, that is, to receive radiation pulses which have not travelled via the printing-image carrier. The output signal of the second transducer constitutes a reference signal which is used to form a quotient or ratio with the corresponding output signal of the first photoelectric transducer. The relative value obtained in this manner is then used in calculation of the amount of dampening agent.

The diffuse radiation returned from the measuring spot can be directed to the first photoelectric transducer using an optical system which forms an image of the measuring spot on the transducer. The optical system advantageously includes an elliptical reflecting surface or reflector having one focal point which coincides with the measuring spot and another focal point which coincides with the first photoelectric transducer. The output obtained in this manner is such that an adequate signal/noise ratio is achieved even for very short radiation pulses. This makes it possible to eliminate errors due to external disturbances.

The measuring arrangement of the invention may be formed with a window through which radiation enters and leaves the arrangement. This window may be covered with a disc or shield to protect the arrangement against paper dust, dyes and so on. The disc is transparent to radiation of the wavelength used for the measurements. In order to prevent the measurements from being affected by the disc, the disc is designed so as to be substantially non-reflective for radiation of the wavelength used in the measurements.

The novel features which are considered as characteristic of the invention are set forth in particular in the appended claims. The improved measuring arrangement itself, however, both as to its construction and its mode of operation, together with additional features and advantages thereof, will be best understood upon perusal of the following detailed description of certain specific embodiments with reference to the accompanying drawings.

BRIEF DESCRIPTION OF THE DRAWINGS

FIG. 3 is a schematic diagram of a processing circuit forming part of the arrangement of FIG. 1; and FIG. 4 is a schematic diagram illustrating the principal components of another embodiment of the processing circuit.

DESCRIPTION OF THE PREFERRED EMBODIMENTS

Figure 1:
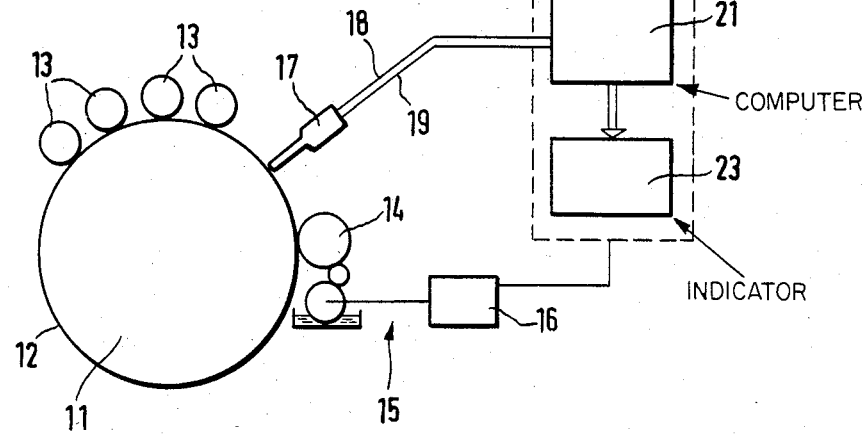
FIG. 1 schematically illustrates the principal components of an arrangement according to the invention as employed for measuring the thickness of a layer of dampening agent on a printing-image carrier of a rotating offset printing press.

FIG. 1 schematically illustrates a plate cylinder 11 which is mounted in a printing station of a rotating offset printing press. The structure of the printing station is conventional and the printing station is therefore not shown in detail. A printing-image carrier 12 is mounted on the plate cylinder 11 in a known manner. Inking rollers 13 of an inking unit which is not fully illustrated bear against the printing-image carrier 12 as does a dampening roller 14 of a schematically illustrated dampening unit which is generally identified by the reference numeral 15. In the present embodiment, the dampening unit 15 is equipped with a variable speed motor 16 in order to permit adjustment of the amount of dampening agent.

A measuring unit or head 17 is mounted in the printing press and is spaced from the printing-image carrier 12 by a small gap. The measuring unit 17 is advantageously movable in a direction parallel to the axis of the plate cylinder 11. A pair of conductors 18 and 19 connect the measuring unit 17 with a processing circuit which is delineated by a dashed box and is generally identified by the reference numeral 20.

The processing circuit 20 includes a computer 21, a working memory 22 and an indicator 23. The indicator 23 displays the measured amount of the dampening agent in a suitable form.

Figure 2:
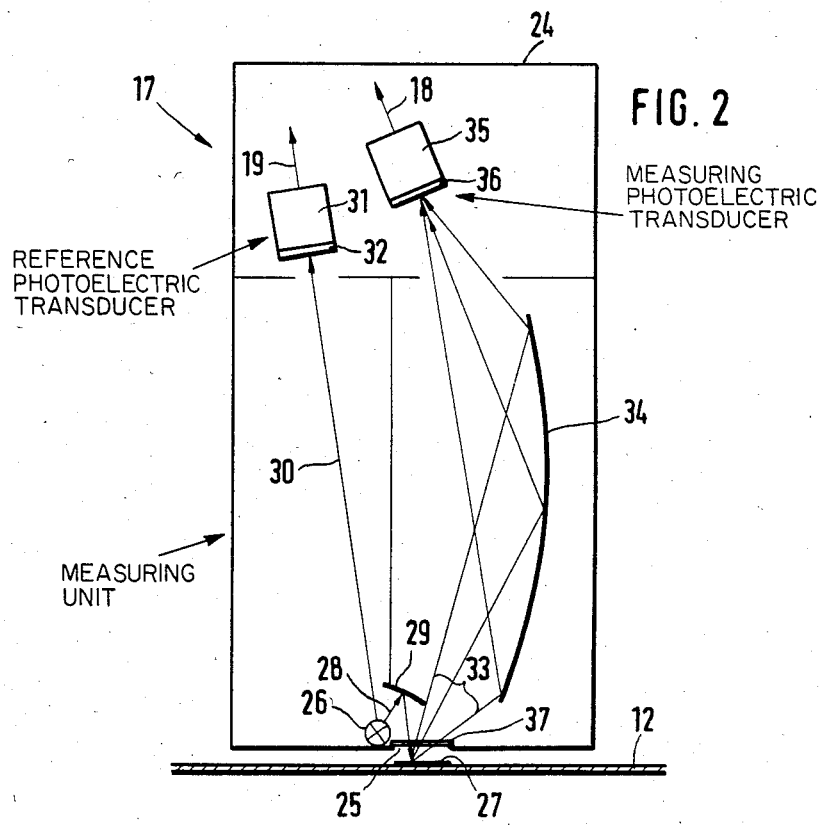
FIG. 2 is a schematic longitudinal cross-sectional view illustrating the principal components of a measuring unit forming part of the arrangement of FIG. 1 and situated adjacent to the printing-image carrier.

FIG. 2 is a simplified longitudinal crosssectional view of the measuring unit 17. The cross section of FIG. 2 is taken in a radial plane of the plate cylinder 11. The measuring unit 17 includes a housing 24 which is tightly sealed except for an opening 25 which permits light to enter and leave the housing 24. The opening 25 is located at the lower end of the housing 24 which faces the printing-image carrier 12. A source 26 of light pulses is located inside the housing 24 and is synchronized with a measuring spot 27 on the printing-image carrier 12 in such a manner that the source 26 is activated and emits a light pulse whenever the measuring spot 27 passes by the opening 25. Since the mode of synchronizing the source 26 and the measuring spot 27 is conventional and does not form part of the invention, no details are presented here.

A portion of each light pulse in the form of a measuring beam 28 is directed onto the measuring spot 27 by means of a reflector 29. Another portion of each light pulse in the form of a reference beam 30 travels directly to a reference detector 31 which is here assumed to be a photoelectric transducer. A filter 32 is located upstream of the reference transducer 31. The filter 32 has a transmission band corresponding to the wavelength which is to be used in measuring the amount of dampening agent on the printing-image carrier 12. This wavelength may be an absorption wavelength of the dampening agent or a wavelength near the absorption wavelength.

Radiation beams 33 returning from the measuring spot 27 outside of the angle of reflection of the beam 28 directed at the measuring spot 27 enter the housing 24 via the opening 25. A reflector 34 concentrates the radiation beams 33 on a measuring detector 35 which is here likewise assumed to be a photoelectric transducer. A filter 36 having the same transmission band as the filter 32 is located upstream of the measuring transducer 35. The reflector 34 is elliptical and is arranged in such a manner that one of its focal points falls on the measuring spot 27 while another focal point falls on the sensitive surface of the measuring transducer 35. This optical arrangement results in a superior output from the radiation which is returned from the measuring spot 27 within a specific return angle.

The opening 25 of the housing 24 is covered by a disc or shield 37 which protects the interior of the housing 24 against dust, ink and the like. The disc 37 is transparent to radiation of the wavelength used for measuring purposes, namely, radiation having the wavelength of the transmission bands of the filters 32 and 36, and is non-reflective for at least such radiation. Accordingly, the disc 37 possesses no optical properties which can influence the measuring procedure.

FIG. 3 shows certain details of the processing circuit 20. The computer 21 includes a dividing unit 41, a pair of adding/subtracting units 42 and 43, and a second dividing unit 44 which is located downstream of the adding/subtracting units 42 and 43. The computer 21 is connected with the working memory 22. The working memory 22 comprises a memory section 221 for the storage of a relative glancing signal $E_g/R_g$ where $E_g$ is a measured glancing signal derived from the measuring transducer 35 and $R_g$ is a reference glancing signal derived from the reference transducer 31. The relative glancing signal $E_g/R_g$ is used to correct for radiation from the measuring beam 28 which glances off rather than passing through the dampening agent on the printing-image carrier 12. The working memory 22 further comprises a memory section 222 for the storage of a relative cross-talk signal $E_c/R_c$ where $E_c$ is a measured cross-talk signal derived from the measuring transducer 35 and $R_c$ is a reference cross-talk signal derived from the reference transducer 31. The relative cross-talk signal $E_c/R_c$ is used to correct for cross-talk. The working memory 22 also includes a memory section 223 for storage of a relative dry signal $E_d/R_d$ where $E_d$ is a measured dry signal obtained from the measuring transducer 35 and $R_d$ is a reference dry signal obtained from the reference transducer 31. The control means and procedures by which the relative signals or values $E_g/R_g$; $E_c/R_c$; $E_d/R_d$ are stored in the respective memory sections 221-223 and introduced into the calculations for the amount of dampening agent are not detailed here since they are known to those skilled in the art.

A value E* which is representative of the amount of dampening agent on the printing-image carrier 12 may be obtained at the output of the divider 44. The value E* may be used, for example, to regulate the dampening unit 15 of a printing press. The value E* is also transmitted to the indicator 23.

The operation of the measuring arrangement is as follows:

The printing-image carrier 12 including the measuring spot 27 is initially dry. Before the start of a printing operation, and while the printing-image carrier 12 is in a dry condition, a radiation pulse is emitted by the radiation source 26 of the measuring unit 17 located adjacent to the printing-image carrier 12. The measuring beam 28 corresponding to the radiation pulse is directed onto the dry measuring spot 27. The radiation beams 33 returned from the measuring spot 27 cause the electrical pulse or signal $E_d$ to be generated at the output of the measuring transducer 35. On the other hand, the reference beam 30 corresponding to the radiation pulse from the source 26 causes the electrical reference pulse or signal $R_d$ to be generated at the output of the reference transducer 31. The signals $E_d$ and $R_d$ are transmitted to the processing circuit 20 via the respective conductors 18 and 19. In the processing circuit 20, the relative dry value $E_d/R_d$ is formed in the divider 41 and then stored in the memory section 223 of the working memory 22 for use during the subsequent printing operation.

Once the relative dry signal $E_d/R_d$ has been established, an excess of dampening agent is applied to the printing-image carrier 12. Another radiation pulse is then emitted by the radiation source 26 and the corresponding measuring beam 28 is directed onto the measuring spot 27. In this case, the radiation returned from the measuring spot 27 in the form of the radiation beams 33 is radiation which glances off the surface of the dampening agent rather than radiation which has passed through the dampening agent and been returned from the measuring spot 27 per se. The radiation beams 33 cause the measuring transducer 35 to generate the glancing signal $E_g$. The reference beam 30 corresponding to the radiation pulse which generated the glancing signal $E_g$ causes the reference transducer 31 to generate the reference glancing signal $R_g$. The glancing signal $E_g$ and the reference glancing signal $R_g$ are transmitted to the processing circuit 20 via the respective conductors 18 and 19. The relative glancing value $E_g/R_g$ is formed in the divider 41 and then stored in the memory section 221 of the working memory 22 for use during the subsequent printing operation.

In order to compensate for unavoidable errors inherent in the measuring unit 17, cross-talk signals may be generated by substituting a black body for the measuring spot 27. A radiation pulse is then generated by the radiation source 26 and the corresponding measuring beam 28 is directed onto the black body. Any radiation beams 33 returned from the black body cause the measuring transducer 35 to generate the cross-talk signal $E_c$. The reference beam 30 corresponding to the radiation pulse which generated the cross-talk signal $E_c$ causes the reference transducer 31 to generate the reference cross-talk signal $R_c$. The cross-talk signal $E_c$ and the reference cross-talk signal $R_c$ are transmitted to the processing circuit 20 via the respective conductors 18 and 19. The relative cross-talk value $E_c/R_c$ is formed in the divider 41 and then stored in the memory section 222 of the working memory 22 for use as a correction factor in the measurements to be subsequently performed during the printing operation in order to determine the amount of dampening agent on the printing-image carrier 12.

The actual measurement of the amount of dampening agent on the printing-image carrier 12 is performed during operation of the printing press when the printing-image carrier 12 is dampened by the dampening roller 14 of the dampening unit 15. The radiation source 26 is regulated so that a radiation pulse is emitted at such an instant during each revolution of the plate cylinder 11, or once during a predetermined number of revolutions of the plate cylinder 11, that the corresponding measuring beam 28 impinges upon the measuring spot 27. The manner in which the radiation source 26 is synchronized with the printing-image carrier 12 and the associated measuring spot 27 is well-known to those skilled in the art and therefore need not be described here in detail. The radiation beams 33 corresponding to each radiation pulse cause the measuring transducer 35 to generate the damp signal E. The reference beam 30 corresponding to each radiation pulse causes the reference transducer 31 to generate the reference damp signal R. The damp signal E and the reference damp signal R are transmitted to the processing circuit 20 via the respective conductors 18 and 19. In the most general form, the computer 21 calculates a value E* representative of the amount of dampening agent on the printing-image carrier 12 taking into account all of the relative values $E_g/R_g; E_c/R_c; E_d/R_d$ which were previously measured and stored in the respective memory sections 221-223 of the working memory 22. The value E* is obtained from the following equation:

$$E^* = [E/R - E_c/R_c - E_g/R_g]/[E_d/R_d - E_c/R_c].$$

Due to the simplicity of the calculation, a flow diagram illustrating the manner of performing the same is unnecessary.

An approximate value for the amount of dampening agent on the printing-image carrier 12 may be obtained by disregarding the glancing signals $E_g$ and $R_g$; by considering the effect of cross-talk to be negligible and disregarding the cross-talk signals $E_c$ and $R_c$; and, where possible, assuming the radiation source 26 to be absolutely constant. In the coarsest approximation, a value E*' representative of the amount of dampening agent on the printing-image carrier 12 is derived from the following equation:

$$E^{*'} = E/E_d.$$

The simplified processing circuit shown in FIG. 4 is sufficient to process the signals which are required to perform the calculations for the last equation. The processing circuit of FIG. 4 has a memory 224 for storing the dry signal $E_d$ derived from the measuring transducer 35 upon irradiation of the measuring spot 27 while dry as well as a divider 44'. The value E*' appears at the output of the divider 44'.

The preceding description illustrates that, on the basis of its substantial technical simplification alone, the measuring arrangement of the invention is superior to the measuring arrangements of the prior art. The preceding description also demonstrates that the amount of dampening agent is determined by relating the damp value E which is affected by the amount of dampening agent to the dry value $E_d$ which may be considered to remain constant at least for a certain time inverval rather than relating E to a comparative value which is likewise affected by the amount of dampening agent. Since the dry value $E_d$ changes slightly with the degree of wear of the printing-image carrier 12, the dry value $E_d$ is constantly updated during interruptions in the printing operation by renewed measurements on the printing-image carrier 12 while dry.

Without further analysis, the foregoing will so fully reveal the gist of the present invention that others can, by applying current knowledge, readily adapt it for various applications without omitting features that, from the standpoint of prior art, fairly constitute essential characteristics of the generic and specific aspects of our contribution to the art and, therefore, such adaptations should and are intended to be comprehended within the meaning and range of equivalence of the appended claims.

We claim:

1. An arrangement for determining the amount of dampening agent on a printing-image carrier, said arrangement comprising:
  (a) a radiation source for directing radiation at the carrier;
  (b) first means for generating first signals in response to radiation which returns from the carrier add has a predetermined wavelength at least approximating an absorption wavelength of the dampening agent; and
  (c) second means for generating second signals representative of the amount of dampening agent on the carrier, said second means being arranged to receive said first signals and to relate a preselected first signal generated while the carrier is substantially dry to another first signal generated while the carrier is damp, and said second means being designed such that the second signals are derived from the relationship between said preselected and other first signals, said second means being further arranged to receive and process a glancing signal so as to compensate for errors due to radiation which is directed towards the carrier from said source and glances off the dampening agent applied to the carrier.

2. An arrangement as defined in claim 1, wherein said second means comprises memory means for storing said preselected first signal.

3. An arrangement as defined in claim 2, wherein said memory means comprises a working memory.

4. An arrangement as defined in claim 1, wherein said source is arranged to irradiate a predetermined region of the carrier.

5. An arrangement as defined in claim 1, wherein the carrier is rotatably mounted in an offset printing press.

6. An arrangement as defined in claim 1, wherein said source is arranged to emit radiation in pulses.

7. An arrangement as defined in claim 1, wherein said source is arranged to irradiate the carrier during printing, said first and second means being arranged to generate said signals during printing.

8. An arrangement as defined in claim 1, wherein said first means comprises a photoelectric transducer.

9. An arrangement as defined in claim 1, wherein said first means is arranged to detect radiation returned outside of the angle of reflection of the radiation which impinges on the carrier from said source.

10. An arrangement as defined in claim 1, wherein said second means is arranged to receive and process a cross-talk signal so as to compensate for errors due to cross-talk.

11. An arrangement as defined in claim 10, wherein said second means comprises memory means for storing said preselected and cross-talk signals.

12. An arrangement as defined in claim 1, wherein said second means comprises memory means for storing said preselected and glancing signals.

13. An arrangement as defined in claim 1, comprising additional means for generating reference signals in response to radiation of said predetermined wavelength which impinges upon said additional means directly from said source, said second means being arranged to receive said reference signals and to form ratios of said preselected and other signals with respective ones of said reference signals.

14. An arrangement as defined in claim 13, wherein said additional means comprises a photoelectric transducer.

15. An arrangement as defined in claim 13, wherein said second means comprises memory means for storing said reference signals.

16. An arrangement as defined in claim 13, wherein said source is arranged to emit radiation in pulses and said preselected signal and its respective reference signal are derived from the same pulse, said other signal and its respective reference signal also being derived from the same pulse.

17. An arrangement as defined in claim 13, wherein said second means is arranged to receive and process at least one cross-talk signal so as to compensate for errors due to cross-talk, said additional means being arranged to generate a reference cross-talk signal, and said second means being designed to receive said reference cross-talk signal and to form a ratio between said one and reference cross-talk signals.

18. An arrangement as defined in claim 17, wherein said source is arranged to emit radiation in pulses and said one and reference cross-talk signals are derived from the same pulse.

19. An arrangement as defined in claim 1, comprising a reflector for directing radiation returned from the carrier towards said first means, said reflector having a pair of focal points including one which coincides with the carrier and another which coincides with said first means.

20. An arrangement as defined in claim 19, wherein said reflector is substantially elliptical.

21. An arrangement as defined in claim 1, wherein said source and said first means are incorporated in a unit and shielding means is provided to shield said unit against contamination, said shielding means being transparent to and substantially non-reflective for radiation of said predetermined wavelength.

22. An arrangement as defined in claim 21, wherein said shielding means comprises a disc.

23. An arrangement as defined in claim 21, wherein said unit comprises a reflector for directing radiation returned from the carrier to said first means.

24. An arrangement for determining the amount of dampening agent on a printing-image carrier, said arrangement comprising:
(a) A radiator source for directing radiation at the carrier;
(b) first means for generating first signals in response to radiation which returns from the carrier and has a predetermined wavelength at least approximating an absorption wavelength of the dampening agent;
(c) second means for generating second signals representative of the amount of dampening agent on the carrier, said second means being arranged to receive said first signals and to relate a preselected first signal generated while the carrier is substantially dry to another first signal generated while the carrier is damp, and said second means being designed such that the second signals are derived from the relationship between said preselected and other first signals, said second means being further arranged to receive and process at least one glancing signal so as to compensate for errors due to radiation which is directed towards the carrier from said source and glances off the dampening agent applies to the carrier; and
(d) additional means for generating reference signals in response to radiation of said predetermined wavelength which impinges upon said additional means directly from said source, said second means being arranged to receive said reference signals and to form ratios of said preselected and other signals with respective ones of said reference signals, and said additional means being designed to generate a reference glancing signal, said second means being arranged to receive said reference glancing signal and to form a ratio between said one and reference glancing signals.

25. An arrangement as defined in claim 24, wherein said source is arranged to emit radiation in pulses and said one and reference glancing signals are derived from the same pulse.

26. A method of determining the amount of dampening agent on a printing-image carrier, said method comprising the steps of:
(a) irradiating said carrier;
(b) measuring a characteristic of radiation of a predetermined wavelength returned from said carrier while substantially dry to obtain at least one dry value of said characteristic, said predetermined wavelength at least approximating an absorption wavelength of said dampening agent;
(c) applying said dampening agent to said carrier;
(d) measuring said characteristic for radiation of said predetermined wavelength returned from said carrier while damp to obtain at least one damp value of said characteristic;
(e) establishing a relationship between said dry and damp values;
(f) generating a signal based on said relationship and representative of the amount of dampening agent on said carrier; and
(g) correcting for radiation which glances off said dampening agent.

27. A method as defined in claim 26, comprising the steps of measuring a dry reference value and a damp reference value of said characteristic; and establishing ratios between said dry reference value and said one dry value and between said damp reference value and said one damp value, the step of establishing said relationship being performed with said ratios.

28. A method as defined in claim 26, comprising the step of correcting for cross-talk.

29. A method as defined in claim 28, wherein the step of correcting for cross-talk comprises the operations of obtaining an actual and a reference crosstalk value; and establishing a ratio between said actual and reference cross-talk values.

30. A method as defined in claim 26, wherein the step of correcting for glancing radiation comprises the operations of obtaining an actual and a reference glancing value; and establishing a ratio between said actual and reference glancing values.

31. A method as defined in claim 26, wherein the measuring steps are performed for radiation returned from said carrier outside of the angle of reflection of the radiation directed at said carrier during the irradiating step.

32. A method as defined in claim 26, wherein the correcting step comprises generating a glancing signal by applying an excess of said dampening agent to said carrier, and irradiating the latter while said excess is on said carrier.

* * * * *